United States Patent
Schiffler et al.

(10) Patent No.: US 9,402,838 B2
(45) Date of Patent: *Aug. 2, 2016

(54) PHENOXYETHYL PIPERIDINE COMPOUNDS

(71) Applicant: Eli Lilly and Company, Indianapolis, IN (US)

(72) Inventors: Matthew Allen Schiffler, Indianapolis, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/595,350

(22) Filed: Jan. 13, 2015

(65) Prior Publication Data

US 2015/0126555 A1    May 7, 2015

Related U.S. Application Data

(63) Continuation of application No. 13/922,278, filed on Jun. 20, 2013, now Pat. No. 8,962,659.

(60) Provisional application No. 61/779,099, filed on Mar. 13, 2013, provisional application No. 61/665,951, filed on Jun. 29, 2012.

(51) Int. Cl.
*A61K 31/445*  (2006.01)
*C07D 211/60*  (2006.01)
*A61K 45/06*  (2006.01)

(52) U.S. Cl.
CPC ............... *A61K 31/445* (2013.01); *A61K 45/06* (2013.01); *C07D 211/60* (2013.01)

(58) Field of Classification Search
CPC ... C07D 210/60; C07D 211/60; A61K 31/445
USPC .......................................... 514/330; 546/225
See application file for complete search history.

(56) References Cited

U.S. PATENT DOCUMENTS

| | | |
|---|---|---|
| 7,271,183 B2 | 9/2007 | Elworthy |
| 7,414,071 B2 | 8/2008 | Cameron et al. |
| 7,534,914 B2 | 5/2009 | Koike et al. |
| 7,592,364 B2 | 9/2009 | Old et al. |
| 8,598,355 B2 | 12/2013 | Nozawa |
| 8,962,659 B2 * | 2/2015 | Schiffler et al. ............... 514/330 |
| 2005/0250818 A1 | 11/2005 | Koike et al. |
| 2011/0136887 A1 | 6/2011 | Yuan |

FOREIGN PATENT DOCUMENTS

| | | |
|---|---|---|
| GB | 1538482 | 1/1979 |
| WO | 2005021508 A1 | 3/2005 |
| WO | 2005105732 A1 | 11/2005 |
| WO | 2005105733 A1 | 11/2005 |
| WO | 2007121578 A1 | 11/2007 |
| WO | 2007143825 A1 | 12/2007 |
| WO | 2011102149 A1 | 8/2011 |
| WO | 2013004290 A1 | 1/2013 |
| WO | 2013004291 A1 | 1/2013 |

OTHER PUBLICATIONS

Document (Office action of U.S. Appl. No. 13/922,278, allowed case) p. 1-6 (2014).*
Barriello et al., "Preparation of cyclic amine . . . " CA158:158421 (2013).

* cited by examiner

*Primary Examiner* — Celia Chang
(74) *Attorney, Agent, or Firm* — Nelson L. Lentz

(57) ABSTRACT

The present invention provides a compound of the Formula II:

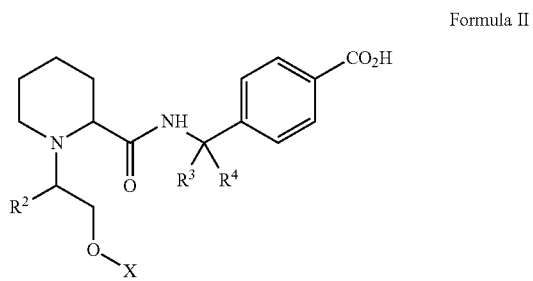

Formula II wherein X is:

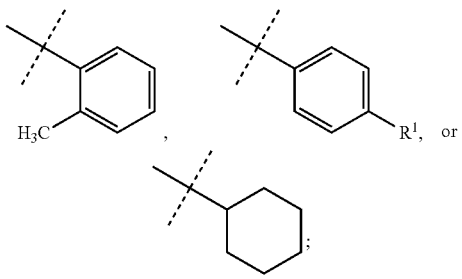

$R^1$ is H, —CN, or F;
$R^2$ is H or methyl;
$R^3$ is H; and
$R^4$ is H, methyl, or ethyl; or
$R^3$ and $R^4$ joined together form a cyclopropyl ring;
or a pharmaceutically acceptable salt thereof.

4 Claims, No Drawings

PHENOXYETHYL PIPERIDINE COMPOUNDS

The present invention relates to novel phenoxyethyl piperidine compounds, to pharmaceutical compositions comprising the compounds, to methods of using the compounds to treat physiological disorders, and to intermediates and processes useful in the synthesis of the compounds.

The present invention is in the field of treatment of inflammatory conditions, such as arthritis, including osteoarthritis and rheumatoid arthritis, and further including pain associated with these conditions. Arthritis affects millions of patients in the United States alone and is a leading cause of disability. Treatments often include NSAIDs (nonsteroidal anti-inflammatory drugs) or COX-2 inhibitors, which may produce untoward cardiovascular and/or gastrointestinal side effects. As such, patients who have a poor cardiovascular profile, such as hypertension, may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3, and EP4. It has been disclosed that EP4 is the primary receptor involved in joint inflammatory pain in rodent models of rheumatoid arthritis and osteoarthritis (See, for example, *J. Pharmacol. Exp. Ther.*, 325, 425 (2008)). Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors. (See, for example, *Bioorganic & Medicinal Chemistry Letters*, 21, 484 (2011)).

WO 2013/004290 discloses cyclic amine derivatives as EP4 receptor antagonists. US 2005/0250818 discloses certain ortho substituted aryl and heteroaryl amide compounds that are EP4 receptor selective antagonists with analgesic activity. In addition, WO 2011/102149 discloses certain compounds that are selective EP4 antagonists which are useful in treating IL-23 mediated diseases.

The present invention provides novel compounds that are selective inhibitors of EP4 relative to EP1, EP2, and EP3. In addition, the present invention provides novel compounds with the potential for reduced cardiovascular or gastrointestinal side effects in comparison to traditional NSAIDs.

Accordingly, the present invention provides a compound of the Formula II:

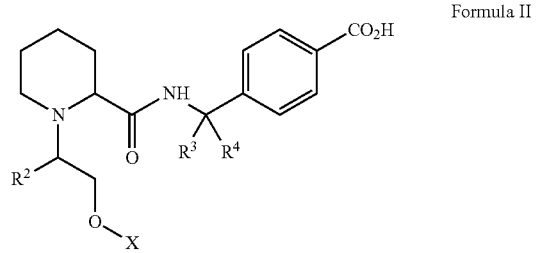

Formula II wherein X is:

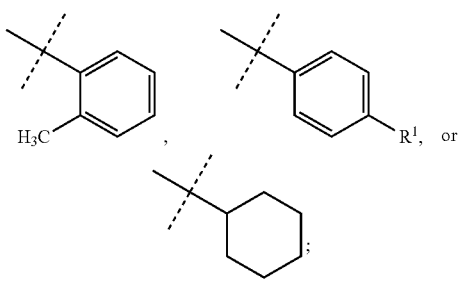

$R^1$ is H, —CN, or F;
$R^2$ is H or methyl;
$R^3$ is H; and
$R^4$ is H, methyl, or ethyl; or
$R^3$ and $R^4$ joined together form a cyclopropyl ring;
or a pharmaceutically acceptable salt thereof.

The present invention further provides a compound of the Formula I:

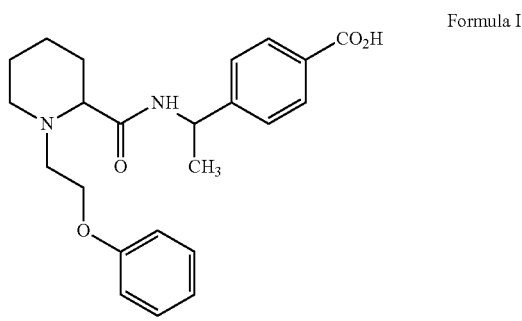 [SMILES: CC(NC(=O)C1CCCCN1CCOc1ccccc1)c1ccc(C(=O)O)cc1]

Formula I or a pharmaceutically acceptable salt thereof.

The present invention also provides a method of treating arthritis in a patient, comprising administering to a patient in need of such treatment an effective amount of a compound of Formula I or Formula II, or a pharmaceutically acceptable salt thereof. The present invention also provides a method of treating osteoarthritis in a patient, comprising administering to a patient in need of such treatment an effective amount of a compound of Formula I or Formula II or a pharmaceutically acceptable salt thereof. In addition, the present invention also provides a method of treating rheumatoid arthritis in a patient, comprising administering to a patient in need of such treatment an effective amount of a compound of Formula I or Formula II, or a pharmaceutically acceptable salt thereof. The present invention also provides a method of treating pain associated with arthritis in a patient, comprising administering to a patient in need of such treatment an effective amount of a compound of Formula I or Formula II, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I or Formula II, or a pharmaceutically acceptable salt thereof.

Furthermore, the invention provides a compound of Formula I or Formula II, or a pharmaceutically acceptable salt thereof for use in therapy, in particular for the treatment of osteoarthritis. In addition, the invention provides a compound of Formula I or Formula II, or a pharmaceutically acceptable salt thereof for use in the treatment of rheumatoid arthritis. The invention also provides a compound or pharmaceutically acceptable salt thereof for use in the treatment of pain associated with osteoarthritis or rheumatoid arthritis. Furthermore, the invention provides the use of a compound of Formula I or Formula II, or a pharmaceutically acceptable salt thereof, for the manufacture of a medicament for the treatment of osteoarthritis. The invention provides the use of a compound of Formula I or Formula II, or a pharmaceutically acceptable salt thereof, for the manufacture of a medicament for the treatment of rheumatoid arthritis. The present invention also provides the use of a compound of Formula I or Formula II or a pharmaceutically acceptable salt thereof, for the manufacture of a medicament for the treatment of pain associated with osteoarthritis or rheumatoid arthritis.

The invention further provides a pharmaceutical composition comprising a compound of Formula I or Formula II, or a pharmaceutically acceptable salt thereof, in combination with one or more pharmaceutically acceptable carriers, diluents, or excipients. In a particular embodiment, the composition further comprises one or more other therapeutic agents. This invention also encompasses novel intermediates and processes for the synthesis of a compound of Formula I or Formula II, or a pharmaceutically acceptable salt thereof.

In addition, the invention includes a method of treating inflammatory conditions such as arthritis, including osteoarthritis and rheumatoid arthritis, in a patient, comprising administering to a patient in need of such treatment an effective amount of an antagonist of a proinflammatory prostaglandin, such as an EP4 antagonist, in combination with an effective amount of a modulator of a lipoxin or resolvin receptor, such as a modulator of BLT-1, BLT-2, ALX/FPR1, GPR32, CysLT1, CysLT2, or ChemR23.

A further aspect of the invention includes a method of treating inflammatory disease such as arthritis, including osteoarthritis and rheumatoid arthritis, in a patient, comprising administering to a patient in need of such treatment an effective amount of an inhibitor of a proinflammatory prostaglandin synthase, such as an mPGES-1 inhibitor, in combination with an effective amount of a modulator of a lipoxin or resolvin receptor, such as a modulator of BLT-1, BLT-2, ALX/FPR1, GPR32, CysLT1, CysLT2, or ChemR23.

As used herein, the terms "treating" or "to treat" includes prohibiting, restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I or Formula II, or pharmaceutically acceptable salt thereof, are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, for example, Remington: The Science and Practice of Pharmacy (D. B. Troy, Editor, 21st Edition, Lippincott, Williams & Wilkins, 2006).

The compounds of Formula I and Formula II are particularly useful in the treatment methods of the invention, but certain groups, substituents, and configurations are preferred for compounds of Formulas I and II. The following paragraphs describe such preferred groups, substituents, and configurations. It will be understood that these preferences are applicable both to the treatment methods and to the new compounds of the invention.

It is preferred that $R^1$ is H, $R^2$ is H, $R^3$ is H, and X is:

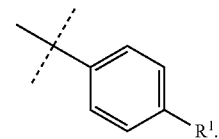

It is further preferred that when $R^3$ is H, that $R^4$ is methyl.
It is further preferred that X is

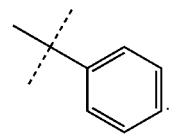

4-[(1S)-1-[[(2R)-1-(2-Phenoxyethyl)piperidine-2-carbonyl]amino]ethyl]benzoic acid of the following structure:

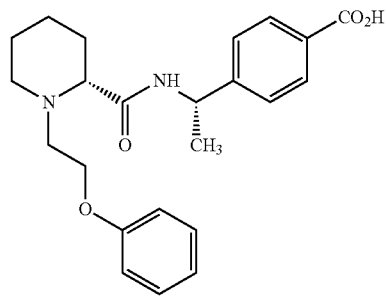 [SMILES: C[C@H](NC(=O)[C@H]1CCCCN1CCOc1ccccc1)c1ccc(C(=O)O)cc1]

and the pharmaceutically acceptable salts thereof are especially preferred.

4-[(1S)-1-[[(2R)-1-(2-phenoxyethyl)piperidine-2-carbonyl]amino]ethyl]benzoic acid hydrochloride is further especially preferred.

As used herein, "kPag" refers to kilopascals gauge; "Boc" refers to a tert-butoxy carbonyl protecting group; "DMEM"

refers to Dulbecco's Modified Eagle's Medium; "ACN" refers to acetonitrile; "DMSO" refers to dimethylsulfoxide; "DMF" refers to N,N-dimethylformamide; "EtOH" refers to ethanol; "THF" refers to tetrahydrofuran; "MeOH" refers to methanol; "EtOAc" refers to ethyl acetate; "Et$_2$O" refers to diethyl ether; "TBME" refers to tort-butyl methyl ether; "BOP" refers to benzotriazol-1-yloxytris(dimethylamino) phosphonium hexafluorophosphate; "NaHMDS" refers to sodium bis(trimethylsilyl)amide; "PGE$_2$" refers to prostaglandin E$_7$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl]ethanesulfonic acid); "HTRF" refers to homogeneous time-resolved fluorescence technology; "HEK" refers to human embryonic kidney; "HBSS" refers to Hank's Balanced Salt Solution; "EC$_{80}$" refers to the concentration of an agent that produces 80% of the maximal efficacy possible for that agent; and "IC$_{50}$" refers to the concentration of an agent that produces 50% of the maximal inhibitory response possible for that agent.

Pharmaceutically acceptable salts and common methodology for preparing them are well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One skilled in the art of synthesis will appreciate that the compounds of Formula I and Formula II are readily converted to and may be isolated as a pharmaceutically acceptable salt, such as a hydrochloride salt, using techniques and conditions well known to one of ordinary skill in the art. In addition, one skilled in the art of synthesis will appreciate that the compounds of Formula I and Formula II are readily converted to and may be isolated as the corresponding free base or free acid from the corresponding pharmaceutically acceptable salt.

The present invention contemplates all individual enantiomers or diastereomers, as well as mixtures of the enantiomers and diastereomers of said compounds including racemates. Individual isomers, enantiomers, or diastereomers may be separated or resolved by one of ordinary skill in the art at any convenient point in the synthesis of compounds of the present invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

The compound of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compound of Formula I, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

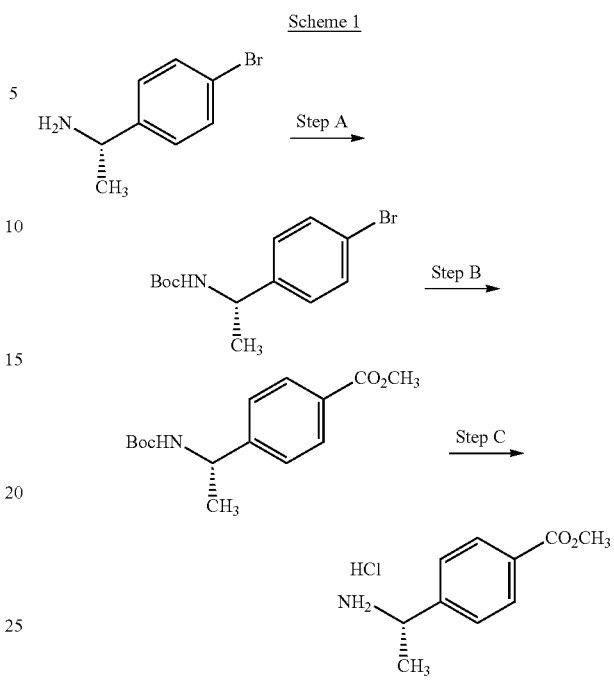

Preparation 1

Synthesis of (S)—N-tert-butoxycarbonyl-1-(4-bromophenyl)ethylamine

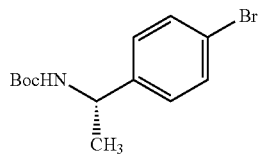 [SMILES: C[C@H](NC(=O)OC(C)(C)C)c1ccc(Br)cc1]

Scheme 1, Step A:

To a stirring solution of (–)-1-(4-bromophenyl)ethylamine (1.00 g, 5.0 mmol) in dichloromethane (10 mL) at 0° C., add di-tert-butyldicarbonate (1.09 g, 5.0 mmol). Allow the reaction mixture to warm to room temperature, then stir for two hours. To the stirring mixture, add 1 M aqueous hydrochloric acid (25 mL), followed by Et$_2$O (25 mL). Separate the layers, and extract the aqueous layer with Et$_2$O (2×25 mL). Combine the organic layers, wash with saturated aqueous NaCl (25 mL), dry the organic layer over MgSO$_4$, filter to remove the solids, and concentrate the filtrate under reduced pressure to furnish the title compound as a white solid (1.50 g, 99% yield). Mass spectrum (m/z) ($^{79}$Br/$^{81}$Br) 244/246 (M+2H–t-Bu)$^+$, 322/324 (M+Na)$^+$. $^1$H NMR (400 MHz, CDCl$_3$): δ 7.46-7.43 (m, 2H), 7.19-7.15 (m, 2H), 4.81-4.65 (m, 1H), 1.48-1.36 (m, 12H).

Prepare the following compound essentially by the method of Preparation 1, using 1-(4-bromophenyl)cyclopropanamine in place of (–)-1-(4-bromophenyl)ethylamine:

| Prep. No. | Chemical Name | Structure | MS (m/z) |
|---|---|---|---|
| 2 | tert-butyl N-[1-(4-bromophenyl)cyclopropyl]carbamate | 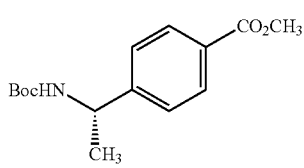 [SMILES: COC(=O)c1ccc([C@H](C)NC(=O)OC(C)(C)C)cc1] | ($^{79}$Br/$^{81}$Br) 256/258 (M + 2H − t-Bu)$^+$, 334/336 (M + Na)$^+$ |

Preparation 3

Synthesis of methyl (S)-4-(1-tert-butoxycarbonylaminoethyl)benzoate

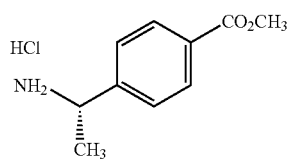

Scheme 1, Step B:

To a Parr autoclave with mechanical stirring, add Pd(OAc)$_2$ (120 mg, 0.53 mmol), 1,1'-bis(diphenylphosphino)ferrocene (355 mg, 0.64 mmol), (S)—N-tert-butoxycarbonyl-1-(4-bromophenyl)ethylamine (1.50 g, 5.0 mmol), anhydrous CH$_3$CN (45 mL), anhydrous CH$_3$OH (30 mL), and triethylamine (1.9 mL, 13.63 mmol). Seal the vessel and pressurize with carbon monoxide to 724 kPag. Heat the vessel to 85° C. and stir the mixture overnight. Vent the reaction vessel (Caution—poison gas!) and transfer to a round-bottomed flask, rinsing with CH$_3$OH. Concentrate the mixture under reduced pressure to furnish an orange residue. Add water (50 mL), then extract with EtOAc (2×50 mL). Wash the combined organic phases with saturated aqueous NaCl (25 mL), then separate the layers, dry the organic phase over MgSO$_4$, filter to remove the solids, and concentrate the filtrate under reduced pressure to give crude product. Purify the product by flash chromatography on silica gel eluting with a gradient of 0% to 60% EtOAc/hexanes. Concentrate the fractions containing the desired product under reduced pressure to furnish the title compound as a white solid (1.00 g, 72% yield). Mass spectrum (m/z) 224 (M+2H−t-Bu)$^+$, 302 (M+Na)$^+$, 581 (2M+Na)$^+$. $^1$H NMR (400 MHz, DMSO-d$_6$): δ 7.89 (d, =8.4 Hz, 2H), 7.41 (d, J=8.2 Hz, 2H), 4.64 (dq, J=7.4, 6.8 Hz, 1H), 3.82 (s, 3H), 1.34 (br s, 9H), 1.28 (d, J=7.2 Hz, 3H).

Prepare the following compound essentially by the method of Preparation 3, using tort-butyl N-[1-(4-bromophenyl)cyclopropyl]carbamate in place of (S)—N-tert-butoxycarbonyl-1-(4-bromophenyl)ethylamine:

| Prep. No. | Chemical Name | Structure | MS (m/z) |
|---|---|---|---|
| 4 | methyl 4-[1-(tert-butoxycarbonylamino)cyclopropyl]benzoate | 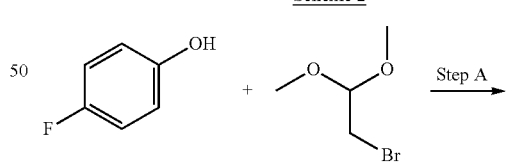 | 236 (M + 2H − t-Bu)$^+$, 314 (M +Na)$^+$, 605 (2M + Na)$^+$ |

Preparation 5

Synthesis of methyl (S)-4-(1-aminoethyl)benzoate hydrochloride

Scheme 1, Step C:

To methyl (S)-4-(1-tert-butoxycarbonylaminoethyl)benzoate (1.00 g, 3.58 mmol), add hydrogen chloride (4 M in dioxane, 5 mL, 20 mmol) and stir the resulting mixture at room temperature for one hour. Concentrate the mixture under reduced pressure to furnish the title compound as a white solid (750 mg, 97% yield). $^1$H NMR (400 MHz, DMSO-d$_6$): δ 8.57 (br s, 3H), 7.99 (d, J=8.4 Hz, 2H), 7.65 (d, J=8.4 Hz, 2H), 4.47 (q, J=6.7 Hz, 1H), 3.84 (s, 3H), 1.50 (d, J=6.8 Hz, 3H).

Prepare the following compound essentially by the method of Preparation 5, using methyl 4-[1-(tert-butoxycarbonylamino)cyclopropyl]benzoate in place of methyl (S)-4-(1-tert-butoxycarbonylaminoethyl)benzoate:

| Prep. No. | Chemical Name | Structure | MS (m/z) |
|---|---|---|---|
| 6 | methyl 4-(1-aminocyclopropyl)benzoate hydrochloride | 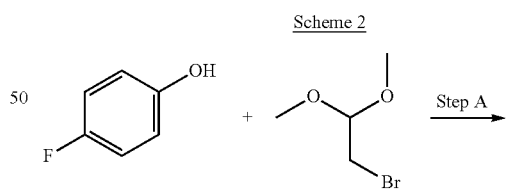 | 192 (M + H)$^+$ |

Scheme 2

-continued

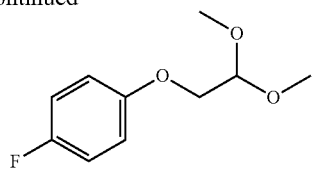

Preparation 7

Synthesis of 1-(2,2-dimethoxyethoxy)-4-fluorobenzene

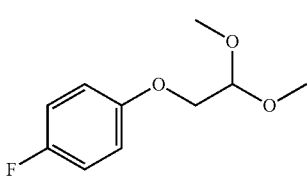

Scheme 2, Step A:

Dissolve 4-fluorophenol (5.5 g, 49.1 mmol) in acetonitrile (49 mL) and treat the solution with 2-bromo-1,1-dimethoxyethane (11.6 mL, 98.1 mmol) and $K_2CO_3$ (16.95 g, 122.7 mmol). Heat the solution to reflux with stirring for five days. Filter the mixture, and concentrate the filtrate under reduced pressure. Subject the resulting crude material to silica gel chromatography eluting with a gradient of 0% to 50% EtOAc/hexanes. Concentrate the fractions containing the desired product under reduced pressure to furnish the title compound as a colorless oil (5.85 g, 60% yield). Mass spectrum (m/z) 218 $(M+NH_4)^+$, 223 $(M+Na)^+$.

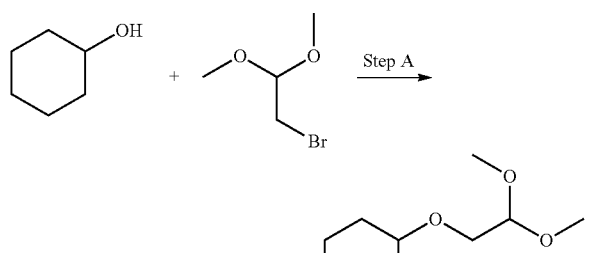

Preparation 8

Synthesis of (2,2-dimethoxyethoxy)cyclohexane

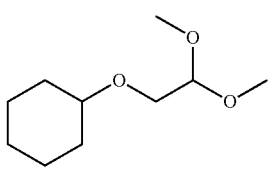

Scheme 3, Step A:

Dissolve cyclohexanol (2.00 mL, 19.1 mmol) in DMF (9.6 mL), then add NaHMDS (1 M solution in THF, 21.0 mL, 21.0 mmol), and stir the solution at room temperature for 5 min. Add 2-bromo-1,1-dimethoxyethane (2.26 mL, 19.1 mmol), then stir the mixture at room temperature under a nitrogen atmosphere for three days. Dilute the mixture with EtOAc (250 mL) and wash with saturated aqueous NaCl (2×250 mL). Dry the organic phase over $MgSO_4$, filter, and concentrate the filtrate under reduced pressure. Subject the resulting crude material to silica gel chromatography eluting with a gradient of 0% to 10% EtOAc/hexanes. Concentrate the fractions containing the desired product under reduced pressure to furnish the title compound as a pale yellow oil (1.10 g, 31% yield). $^1H$ NMR (400 MHz, $CDCl_3$): δ 4.47 (t, J=5.3 Hz, 1H), 3.49 (d, J=5.3 Hz, 2H), 3.39 (s, 6H), 3.25 (tt, J=9.2, 3.7 Hz, 1H), 1.94-1.87 (m, 2H), 1.76-1.69 (m, 2H), 1.55-1.49 (m, 1H), 1.34-1.17 (m, 5H).

Scheme 4

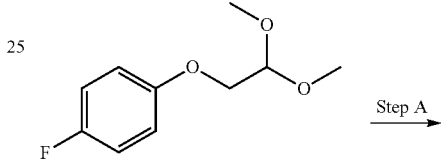

Preparation 9

Synthesis of 2-(4-fluorophenoxy)acetaldehyde

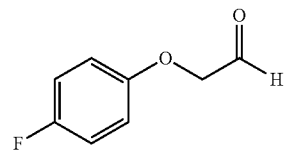 [SMILES: O=CCOc1ccc(F)cc1]

Scheme 4, Step A:

Dissolve 1-(2,2-dimethoxyethoxy)-4-fluorobenzene (1.00 g, 4.99 mmol) in chloroform (5.0 mL) and treat the mixture with trifluoroacetic acid (0.755 mL, 9.99 mmol). Stir the mixture at room temperature for two days, then heat to 65° C. and stir for 4 h. Concentrate the mixture under reduced pressure to furnish the title compound as a colorless oil in ca. 70% purity, as indicated by $^1H$ NMR analysis (550 mg, 71% uncorrected yield). $^1H$ NMR (400 MHz, $CDCl_3$): δ 9.85 (t, J=0.5 Hz, 1H), 7.00 (dd, J=8.9, 8.5 Hz, 2H), 6.85 (dd, J=9.5, 4.3 Hz, 2H), 4.55 (br s, 2H).

Scheme 5

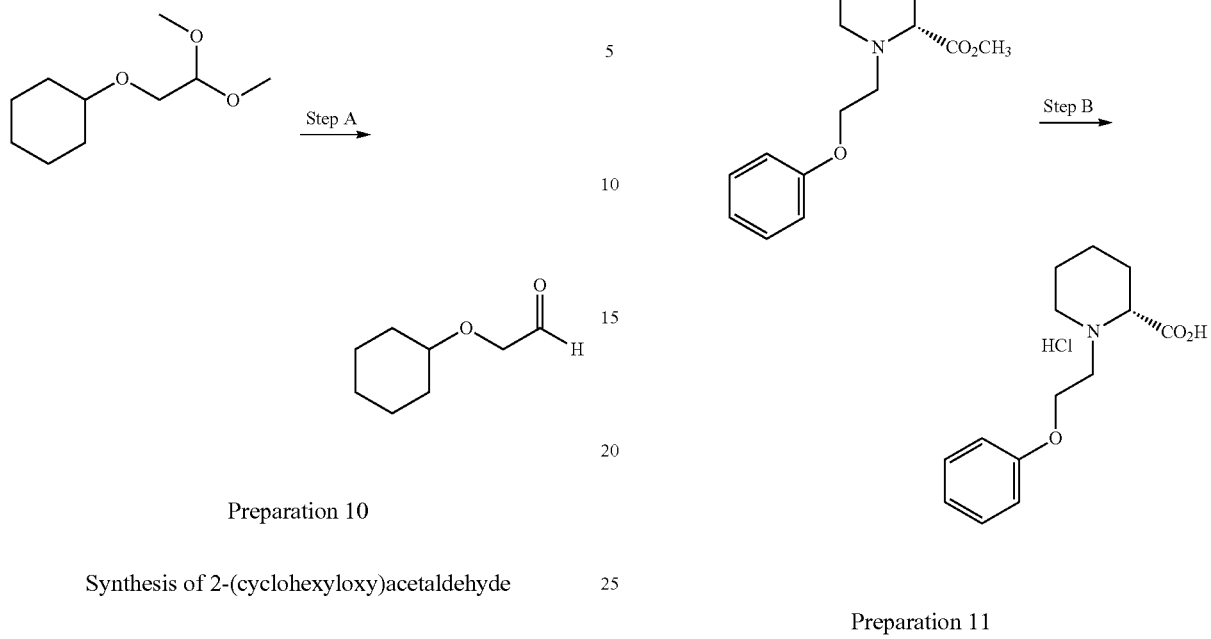

Preparation 10

Synthesis of 2-(cyclohexyloxy)acetaldehyde

Scheme 5, Step A:

Acidify a mixture of (2,2-dimethoxyethoxy)cyclohexane and water (30 mL) to a pH of 1.0 with sulfuric acid (9.0 M aqueous solution), and connect the mixture to a short-path distillation head. Reduce the pressure to 26.7 kPa and heat the mixture to 100° C. for 1 h. Cool the mixture to room temperature, then extract the aqueous layer with TBME (2×75 mL). Wash the combined organic layers with saturated aqueous NaHCO$_3$ (75 mL) and saturated aqueous NaCl (75 mL). Dry the organic phase over MgSO$_4$, filter, and concentrate the filtrate under reduced pressure to furnish the title compound (634 mg, 51% yield). $^1$H NMR (400 MHz, CDCl$_3$): δ 9.73 (t, J=1.0 Hz, 1H), 4.06 (d, J=1.0 Hz, 2H), 3.31 (tt, J=9.2, 3.9 Hz, 1H), 1.95-1.89 (m, 2H), 1.79-1.68 (m, 2H), 1.57-1.50 (m, 1H), 1.39-1.20 (m, 5H).

Scheme 6

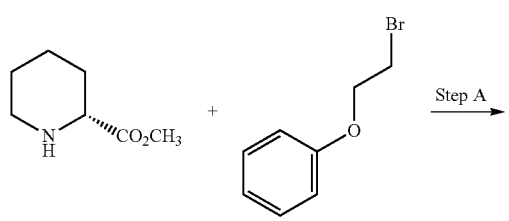 + 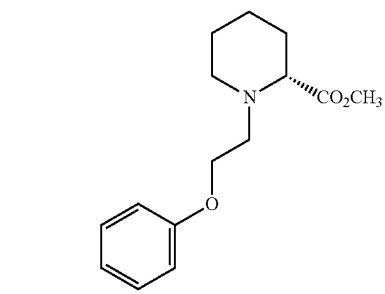 [SMILES: COC(=O)[C@H]1CCCCN1CCOc1ccccc1] Step A

Preparation 11

Synthesis of methyl (R)-1-(2-phenoxyethyl)piperidine-2-carboxylate

Scheme 6, Step A:

Dissolve methyl (R)-piperidine-2-carboxylate (5.00 g, 34.9 mmol) in DMF (87 mL) and treat with K$_2$CO$_3$ (14.48 g, 104.8 mmol) and β-bromophenetole (7.16 g, 34.9 mmol). Stir the mixture overnight at 100° C. Cool the mixture to room temperature and add EtOAc (250 mL). Wash the organic phase with water (4×100 mL) and saturated aqueous NaCl (100 mL). Dry the organic phase over K$_2$CO$_3$, filter to remove the solids, and concentrate the filtrate under reduced pressure to furnish a yellow oil. Subject this crude material to flash chromatography on silica gel eluting with a gradient of 20% to 100% EtOAc/hexanes. Concentrate the fractions containing the desired product under reduced pressure to furnish the title compound as a colorless oil in ca. 90% purity by $^1$H NMR analysis (6.50 g, 64% yield). Mass spectrum (m/z) 264 (M+H)$^+$. $^1$H NMR (400 MHz, CDCl$_3$): δ 7.27 (dd, J=8.5, 7.3 Hz, 2H), 6.93 (t, J=7.3 Hz, 1H), 6.88 (d, J=8.8 Hz, 2H), 4.10 (app t, J=6.1 Hz, 2H), 3.72 (s, 3H), 3.29 (dd, J=8.4, 4.0 Hz, 1H), 3.14 (app dt, J=11.3, 6.4 Hz, 1H), 2.95 (app dt, J=13.7, 6.1 Hz, 1H), 2.89 (app dt, J=13.7, 6.1 Hz, 1H), 2.42 (ddd, J=11.6, 7.9, 3.7 Hz, 1H), 1.90-1.82 (m, 1H), 1.79 (app td, J=8.9, 3.8 Hz, 1H), 1.67-1.59 (m, 3H), 1.39 (app td, J=8.8, 4.0 Hz, 1H).

Preparation 12

Synthesis of (R)-1-(2-phenoxyethyl)piperidine carboxylic acid hydrochloride

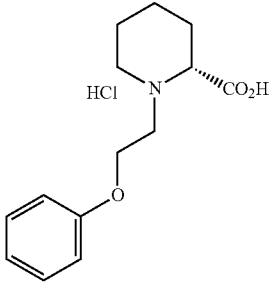 [SMILES: O=C(O)[C@H]1CCCCN1CCOc1ccccc1 ; Cl]

Scheme 6, Step B:

At room temperature, dissolve methyl (R)-1-(2-phenoxyethyl)piperidine-2-carboxylate (6.50 g, 22.2 mmol) in THF (11.1 mL) and add NaOH (5 M aqueous solution, 8.89 mL, 44.4 mmol) and heat to 65° C. overnight with stirring. Add hydrogen chloride (5 M aqueous solution) until the pH of the aqueous phase reaches 1.0. Wash the aqueous phase with $CH_2Cl_2$ (3×75 mL). Concentrate the aqueous phase under reduced pressure to furnish a white solid. Triturate the solid with EtOH (50 mL), filter to remove the suspended salts, and concentrate the filtrate under reduced pressure to furnish the title compound as a white solid (5.17 g, 81% yield). Mass spectrum (m/z) 250 $(M+H)^+$. $^1H$ NMR (400 MHz, $CD_3OD$): δ 7.31 (dd, J=8.8, 7.5 Hz, 2H), 7.02-6.97 (m, 3H), 4.47 (AB-coupled ddd, J=11.5, 7.1, 3.0 Hz, 1H), 4.38 (AB-coupled ddd, J=11.8, 6.3, 3.1 Hz, 1H), 4.15 (dd, J=11.2, 2.8 Hz, 1H), 3.80 (d, J=12.2 Hz, 1H), 3.73-3.68 (m, 2H), 3.29 (app td, J=13.2, 3.8 Hz, 1H), 2.35 (d, J=13.5 Hz, 1H), 2.00-1.80 (m, 4H), 1.68 (app t, J=13.1 Hz, 1H).

Scheme 7

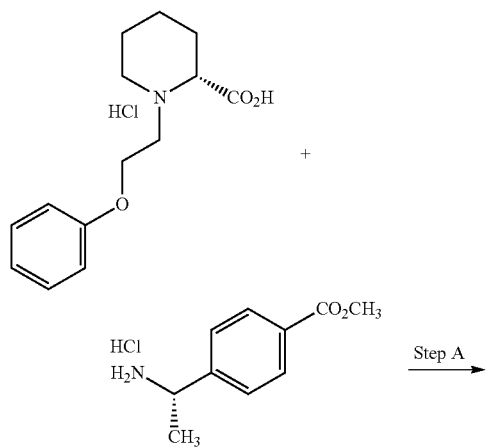

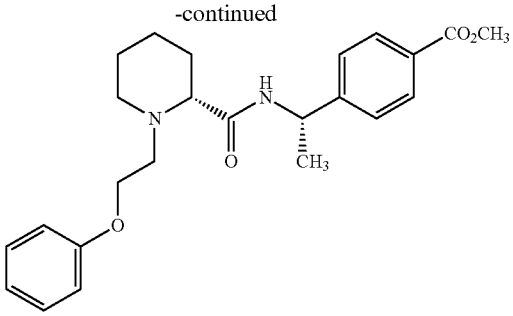

Preparation 13

Synthesis of methyl 4-[(1S)-1-[[(2R)-1-(2-phenoxyethyl)piperidine-2-carbonyl]amino]ethyl]benzoate

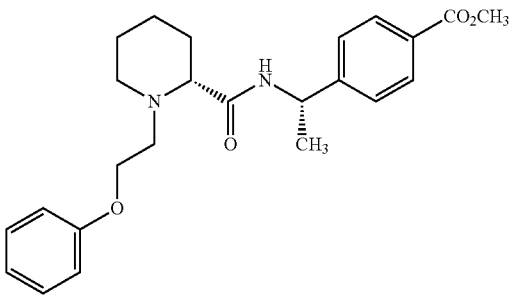

Scheme 7, Step A:

Dissolve (R)-1-(2-phenoxyethyl)piperidine carboxylic acid hydrochloride (750 mg, 2.62 mmol) and methyl (S)-4-(1-aminoethyl)benzoate hydrochloride (566 mg, 2.62 mmol) in DMF (5.25 mL) at room temperature. Add triethylamine (1.65 mL, 11.81 mmol), then BOP (1.51 g, 3.41 mmol). Stir the mixture at room temperature for 3 h, then dilute with EtOAc (25 mL). Wash the mixture with saturated aqueous LiCl (2×25 mL). Dry the organic layer over $MgSO_4$, filter to remove the solids, and concentrate under reduced pressure. Subject the resulting yellow-orange oil to flash chromatography on silica gel, eluting with a gradient of 0% to 100% EtOAc/hexanes. Concentrate the fractions containing the desired product under reduced pressure to provide the title compound as a white solid (930 mg, 86% yield). Mass spectrum (m/z) 411 $(M+H)^+$. $^1H$ NMR (400 MHz, DMSO-$d_6$): δ 8.13 (d, J=8.0 Hz, 1H), 7.86 (d, J=8.3 Hz, 2H), 7.43 (d, J=8.3 Hz, 2H), 7.24 (dd, J=8.8, 7.4 Hz, 2H), 6.89 (t, J=8.3 Hz, 1H), 6.85 (dd, J=8.8, 1.0 Hz, 2H), 4.96 (app pentet, J=7.2 Hz, 1H), 4.05-3.98 (m, 2H), 3.82 (s, 3H), 3.11 (app dt, J=11.4, 3.7 Hz, 1H), 2.81 (dd, J=7.2, 2.8 Hz, 1H), 2.77 (app q, J=6.8 Hz, 1H), 2.50 (app dt, J=11.2, 6.8 Hz, 1H), 2.15 (app td, J=11.6, 2.8 Hz, 1H), 1.68-1.61 (m, 2H), 1.59-1.40 (m, 3H), 1.36 (d, J=7.0 Hz, 3H), 1.27-1.18 (m, 1H).

Prepare the following compounds essentially by the method of Preparation 13, using the appropriate ammonium salts in place of methyl (S)-4-(1-aminoethyl)benzoate hydrochloride:

| Prep. No. | Chemical Name | Structure | MS (m/z) |
|---|---|---|---|
| 14 | methyl 4-[[[(2R)-1-(2-phenoxyethyl)piperidine-2-carbonyl]amino]methyl]benzoate | 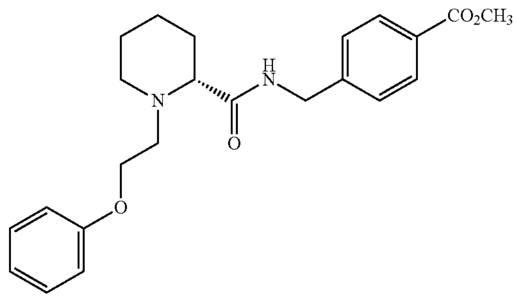 [SMILES: COC(=O)c1ccc(CNC(=O)[C@H]2CCCCN2CCOc2ccccc2)cc1] | 397 (M + H)+ |
| 15 | methyl 4-[(1S)-1-[[(2R)-1-(2-phenoxyethyl)piperidine-2-carbonyl]amino]propyl]benzoate | 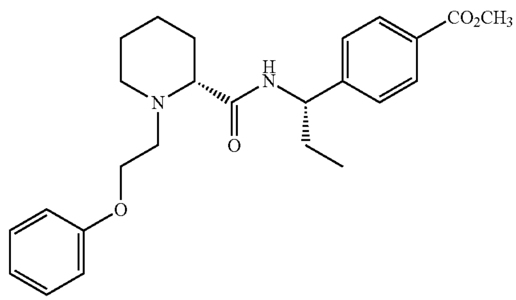 [SMILES: CC[C@H](NC(=O)[C@H]1CCCCN1CCOc1ccccc1)c1ccc(C(=O)OC)cc1] | 425 (M + H)+ |
| 16 | methyl 4-[1-[[(2R)-1-(2-phenoxyethyl)piperidine-2-carbonyl]amino]cyclopropyl]benzoate | 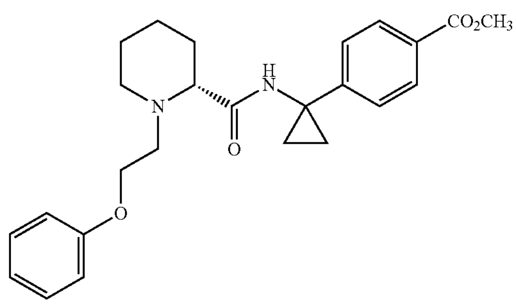 [SMILES: COC(=O)c1ccc(C2(NC(=O)[C@H]3CCCCN3CCOc3ccccc3)CC2)cc1] | 423 (M + H)+ |
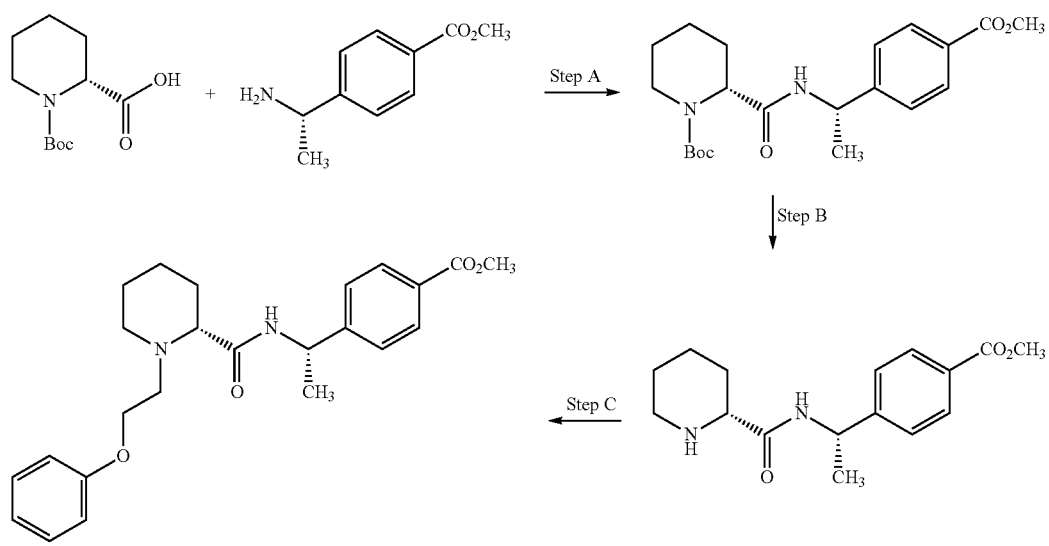
Scheme 8

Preparation 17

Synthesis of methyl 4-[(1S)-[[(2R)-piperidine-1-tert-butoxycarbonyl-2-carbonyl]amino]ethyl]benzoate

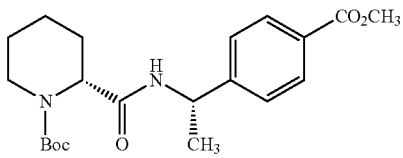 [SMILES: COC(=O)c1ccc([C@H](C)NC(=O)[C@H]2CCCCN2C(=O)OC(C)(C)C)cc1]

Scheme 8, Step A:

To a 0° C. mixture of (R)—N-tert-butoxycarbonylpipecolic acid (20.0 g, 87.2 mmol) and $CH_2Cl_2$ (400 mL), add triethylamine (13.4 mL, 96.0 mmol). Then, add isobutyl chloroformate (12.5 mL, 96.0 mmol) in a dropwise fashion and stir for 20 minutes. Add methyl 4[(S)-aminoethyl]benzoate (17.2 g, 96.0 mmol), then allow the mixture to warm to room temperature and stir for one hour. Add water (300 mL), then separate the layers and wash the organic layer with 1 M aqueous $KHSO_4$ (200 mL), followed by saturated aqueous NaCl (200 mL). Separate the organic layer and dry over $MgSO_4$, then filter to remove the solids and concentrate the filtrate under reduced pressure to furnish the title compound as a colorless oil (34.0 g, 100% yield). Mass spectrum (m/z) 291 (M−Boc+2H)$^+$, 413 (M+Na)$^+$. $^1$H NMR (300 MHz, $CDCl_3$): δ 7.99 (d, J=8.2 Hz, 2H), 7.33 (d, J=8.2 Hz, 2H), 5.14 (app pentet, J=7.1 Hz, 1H), 4.72 s, 1H), 3.90 (s, 3H), 3.40 (dd, J=6.2, 5.8 Hz, 1H), 2.63 (app td, J=6.9, 2.4 Hz, 1H), 2.25 (br s, 1H), 1.75 (app tq, J=13.4, 6.7 Hz, 1H), 1.63-1.50 (m, 3H), 1.47 (s, 9H), 1.38 (app t, J=5.6 Hz, 1H), 0.91 (d, J=6.6 Hz, 3H).

Preparation 18

Synthesis of methyl 4-[(1S)-1-[[(2R)-piperidine-2-carbonyl]amino]ethyl]benzoate

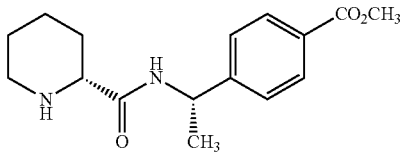 [SMILES: COC(=O)c1ccc([C@H](C)NC(=O)[C@H]2CCCCN2)cc1]

Scheme 8, Step B:

To a 0° C. mixture of EtOAc (136 mL) and EtOH (55.8 mL), add acetyl chloride (62.0 mL, 871 mmol) in a dropwise fashion, then allow the mixture to warm to room temperature over a span of 30 minutes. Add a solution of methyl 4-[(1S)-1-[[(2R)-piperidine-1-tert-butoxycarbonyl-2-carbonyl]amino]ethyl]benzoate (34.0 g, 87.1 mmol) in EtOAc (136 mL), then stir the reaction mixture at room temperature for one hour. Extract the mixture with water (2×100 mL), then add 32% aqueous ammonia solution to the combined aqueous layers until the pH reaches 10. Extract the mixture with TBME (2×200 mL), then dry the combined organic layers over $MgSO_4$, filter to remove the solids, and concentrate the filtrate under reduced pressure to furnish the title compound as a white solid (20.2 g, 80% yield). Mass spectrum (m/z) 291 (M+H)$^+$, 581 (2M+H)$^+$. $^1$H NMR (300 MHz, $CDCl_3$): δ 8.00 (d, J=8.5 Hz, 2H), 7.37 (d, J=8.2 Hz, 2H), 7.15 (br d, J=7.6 Hz, 1H), 5.14 (app pentet, J=7.4 Hz, 1H), 3.90 (s, 3H), 3.23 (dd, J=9.9, 3.3 Hz, 1H), 3.01 (app dt, J=11.8, 3.5 Hz, 1H), 2.68 (ddd, J=12.1, 10.7, 3.0 Hz, 1H), 1.98-1.90 (m, 1H), 1.61-1.52 (m, 1H), 1.48 (d, J=7.1 Hz, 3H), 1.43-1.34 (m, 2H).

Preparation 19

Synthesis of methyl 4-[(1S)-1-[[(2R)-1-(2-phenoxyethyl)piperidine-2-carbonyl]amino]ethyl]benzoate

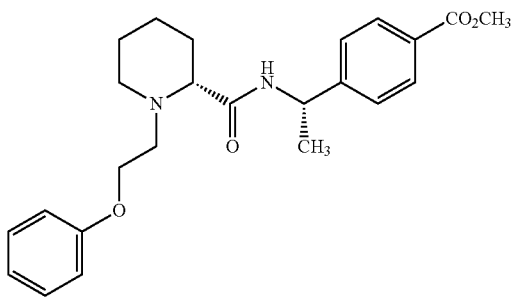

Scheme 8, Step C:

To a suspension of silica gel (100 g) in $CH_2Cl_2$ (705 mL) at room temperature, add a solution of $NaIO_4$ (35.0 g, 161.9 mmol) in water (235 mL) in a dropwise fashion. Stir the mixture for 30 minutes, then add 1,2-dihydroxy-3-phenoxypropane (21.5 g, 121.4 mmol), and stir the mixture for an additional 30 minutes. Filter the mixture to remove the solids, and separate the layers of the filtrate. Dry the organic layer over $MgSO_4$, and filter to remove the solids. To the filtrate, add methyl 4-[(1S)-1-[[(2R)-piperidine-2-carbonyl]amino]ethyl]benzoate (23.5 g, 80.9 mmol), followed by sodium triacetoxyborohydride (35.7 g, 161.9 mmol) in small portions. Stir for one hour at room temperature, then add a 32% aqueous ammonia solution until the pH reaches 10. Separate the layers, and dry the organic phase over $MgSO_4$. Filter to remove the solids, then concentrate the filtrate under reduced pressure to give crude material. Dissolve the material in EtOAc (300 mL) and filter through a pad of silica gel (30 g). Concentrate the filtrate under reduced pressure to furnish 36 g of material. Add TBME (180 mL) and heat to 50° C. While maintaining the temperature at 50° C., add hexanes (360 mL) over 15 minutes, then stir for one hour. Allow the mixture to cool to room temperature, then isolate the solids by filtration and dry under reduced pressure to furnish the title compound as a white solid (16.7 g, 50% yield).

Scheme 9

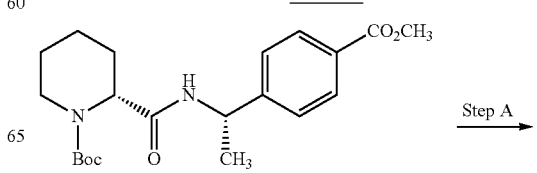

Step A

-continued

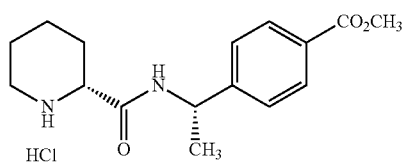

↓ Step B

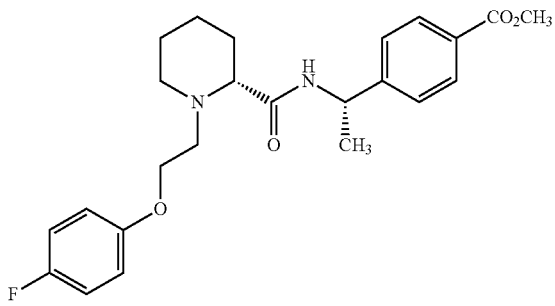

Preparation 20

Synthesis of methyl 4-[(1S)-1-[[(2R)-piperidine-2-carbonyl]amino]ethyl]benzoate hydrochloride

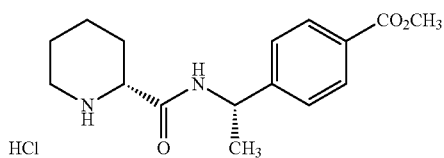 [SMILES: Cl ; COC(=O)c1ccc([C@H](C)NC(=O)[C@H]2CCCCN2)cc1]

Scheme 9, Step A:

Treat methyl 4-[(1S)-1-[[(2R)-piperidine-1-tert-butoxycarbonyl-2-carbonyl]amino]ethyl]benzoate (7.80 g, 19.98 mmol) with hydrochloric acid (4 M solution in 1,4-dioxane, 25.0 mL, 99.9 mmol) and stir the resulting mixture at room temperature for 1 h. Concentrate the mixture under reduced pressure to furnish the title compound as a white solid (6.0 g, 92% yield). Mass spectrum (m/z) 291 (M+H)$^+$, 581 (2M+H)$^+$, 603 (2M+Na)$^+$.

Preparation 21

Synthesis of methyl 4-[(1S)-1-[[(2R)-1-(2-(4-fluorophenoxy)ethyl)piperidine-2-carbonyl]amino]ethyl]benzoate

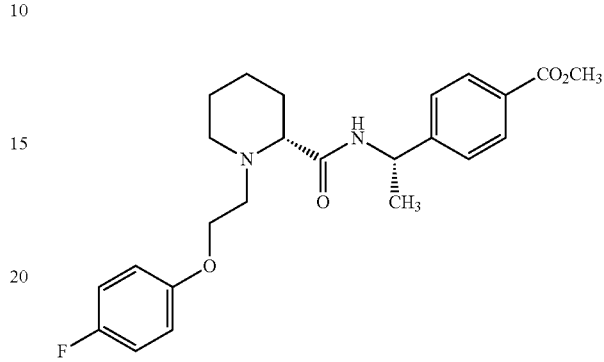

Scheme 9, Step B:

Stir a mixture of methyl 4-[(1S)-1-[[(2R)-piperidine-2-carbonyl]amino]ethyl]benzoate hydrochloride (650 mg, 1.99 mmol) and 2-(4-fluorophenoxy)acetaldehyde (337 mg, 2.19 mmol) in DCE (9.9 mL) at room temperature for 30 min. Add acetic acid (0.113 mL, 1.99 mmol) and sodium triacetoxyborohydride (590 mg, 2.78 mmol) and stir at room temperature for three days. Quench the reaction with saturated aqueous NaHCO$_3$ (25 mL) and extract the aqueous layer with EtOAc (2×25 mL). Wash the combined organic layers with saturated aqueous NaCl (25 mL), then dry the organic phase over MgSO$_4$, filter, and concentrate under reduced pressure. Subject the resulting oil to flash chromatography on silica gel, eluting with a gradient of 0% to 100% EtOAc/hexanes. Concentrate the fractions containing the desired product under reduced pressure to provide the title compound as a white solid (600 mg, 70% yield). Mass spectrum (m/z) 429 (M+H)$^+$, 451 (M+Na)$^+$.

Prepare the following compounds essentially by the method of Preparation 21, using the appropriate aldehydes in place of 2-(4-fluorophenoxy)acetaldehyde:

| Prep. No. | Chemical Name | Structure | MS (m/z) |
|---|---|---|---|
| 22 | methyl 4-[(1S)-1-[[(2R)-1-(2-(4-cyanophenoxy)ethyl)piperidine-2-carbonyl]amino]ethyl]benzoate | 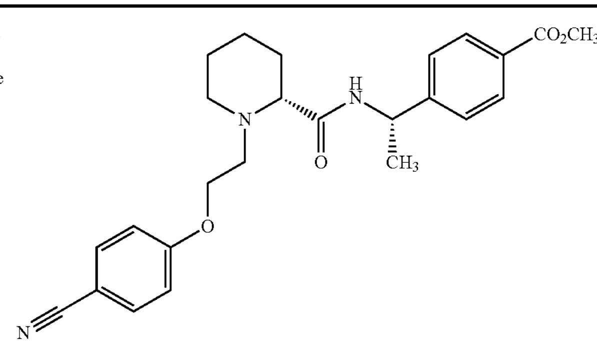 | 436 (M + H)$^+$ |

| Prep. No. | Chemical Name | Structure | MS (m/z) |
|---|---|---|---|
| 23 | methyl 4-[(1S)-1-[[(2R)-1-(2-(2-methylphenoxy)ethyl)piperidine-2-carbonyl]amino]ethyl]benzoate | 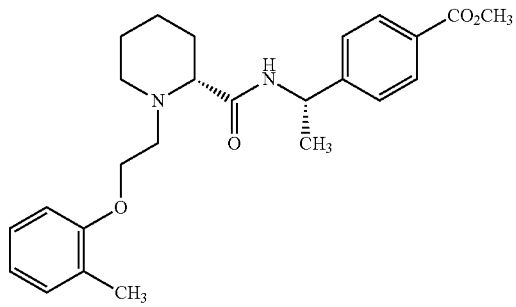 [SMILES: COC(=O)c1ccc([C@H](C)NC(=O)[C@H]2CCCCN2CCOc2ccccc2C)cc1] | 425 (M + H)+, 447 (M + Na)+ |
| 24 | methyl 4-[(1S)-1-[[(2R)-1-(2-cyclohexyloxy ethyl)piperidine-2-carbonyl]amino]ethyl]benzoate | 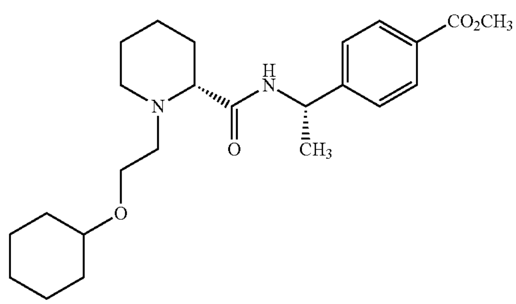 [SMILES: COC(=O)c1ccc([C@H](C)NC(=O)[C@H]2CCCCN2CCOC2CCCCC2)cc1] | 417 (M + H)+, 439 (M + Na)+ |

Preparation 25

Synthesis of methyl 4-[(1S)-1-[[(2R)-1-(1-methyl-2-phenoxyethyl)piperidinium-2-carbonyl]amino]ethyl]benzoate trifluoroacetate

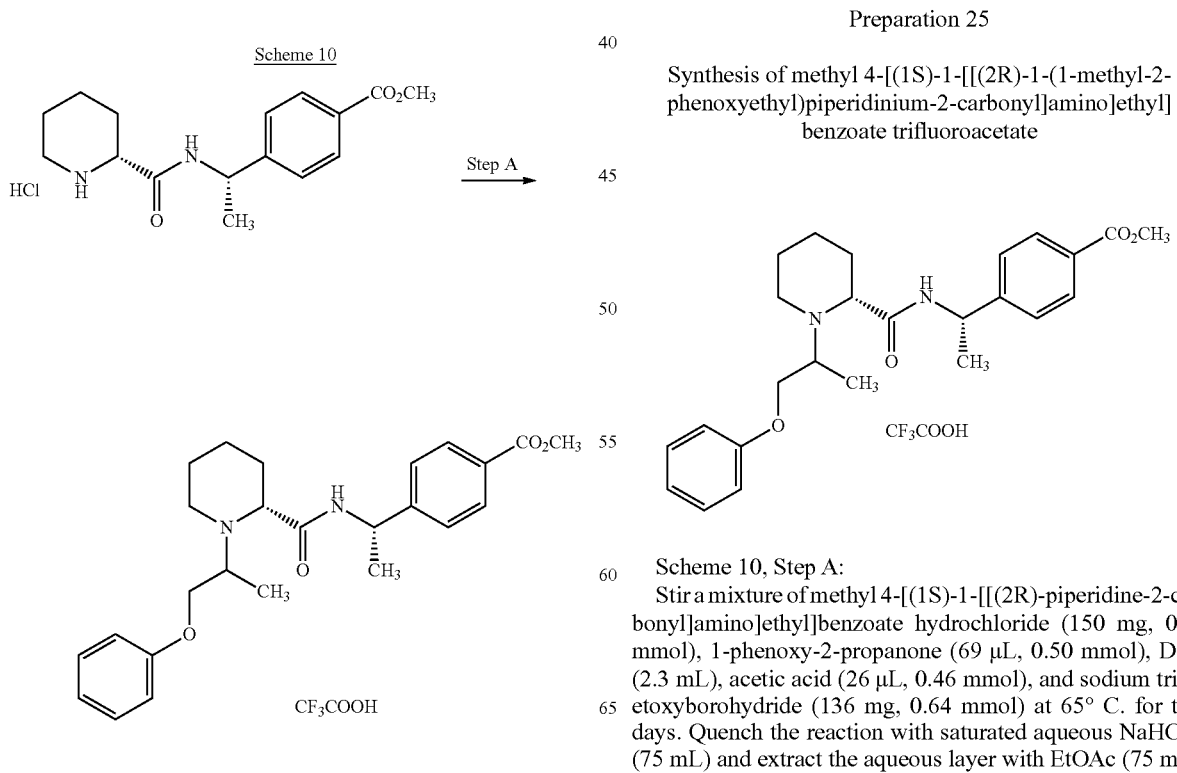

Scheme 10, Step A:

Stir a mixture of methyl 4-[(1S)-1-[[(2R)-piperidine-2-carbonyl]amino]ethyl]benzoate hydrochloride (150 mg, 0.46 mmol), 1-phenoxy-2-propanone (69 μL, 0.50 mmol), DCE (2.3 mL), acetic acid (26 μL, 0.46 mmol), and sodium triacetoxyborohydride (136 mg, 0.64 mmol) at 65° C. for two days. Quench the reaction with saturated aqueous NaHCO₃ (75 mL) and extract the aqueous layer with EtOAc (75 mL).

Dry the organic phase over Na$_2$SO$_4$, filter, and concentrate under reduced pressure. Subject the crude material to reverse-phase chromatography on C18 silica gel, eluting with 0.1% TFA in a gradient of 5% to 50% ACN/water. Concentrate the fractions containing the desired product under reduced pressure to furnish the title compound as a pale yellow oil in a 2:1 mixture of diastereomers (24 mg, 10% yield). Mass spectrum (m/z) 425 (M+H)$^+$.

Scheme 11

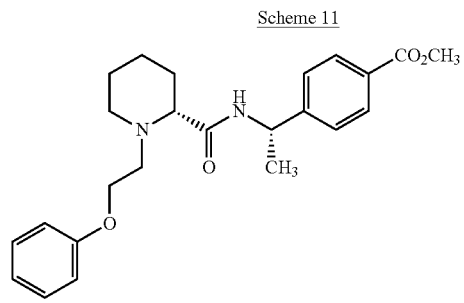

Step A

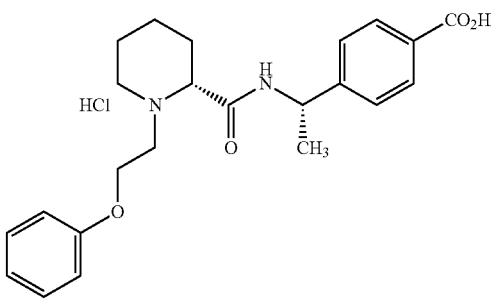

Example 1

EXAMPLE 1

Synthesis of 4-[(1S)-1-[[(2R)-1-(2-phenoxyethyl)piperidine-2-carbonyl]amino]ethyl]benzoic acid hydrochloride

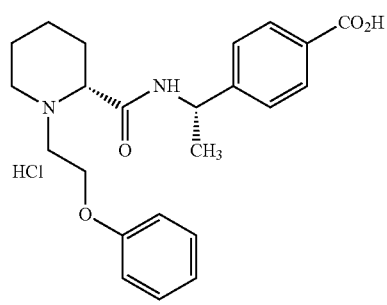 [SMILES: C[C@H](NC(=O)[C@H]1CCCCN1CCOc1ccccc1)c1ccc(C(=O)O)cc1 ; Cl]

Scheme 11, Step A:

Dissolve methyl 4-[(1S)-1-[[(2R)-1-(2-phenoxyethyl)piperidine-2-carbonyl]amino]ethyl]benzoate (930 mg, 2.27 mmol) in THF (4.0 mL) and CH$_3$OH (4.0 mL) at room temperature. Add NaOH (1 M aqueous solution, 4.5 mL, 4.5 mmol), then stir the resulting mixture at room temperature for three days. Concentrate the reaction mixture under reduced pressure to furnish a gummy solid. Add hydrogen chloride (4 M solution in dioxane, 2 mL, 8 mmol), and stir vigorously for 10 minutes. Remove the suspended solids by filtration, and concentrate the filtrate under reduced pressure to furnish a white solid. Triturate the solid in boiling diethyl ether (25 mL), and isolate the suspended solids by filtration to furnish the title compound (650 mg, 66% yield) as a white solid. Mass spectrum (m/z): 397 (M+H)$^+$. $^1$H NMR (400 MHz, DMSO-d$_6$): δ 12.89 (br s, 1H), 10.08 (br s, 1H), 9.41 (d, J=7.6 Hz, 1H), 7.88 (d, J=8.2 Hz, 2H), 7.47 (d, J=8.2 Hz, 2H), 7.26 (dd, J=8.4, 7.6 Hz, 2H), 6.96 (t, J=7.2 Hz, 1H), 6.90 (d, J=7.9 Hz, 2H), 5.02 (app pentet, J=7.1 Hz, 1H), 4.34-4.21 (m, 2H), 4.03 (app t, J=10.2 Hz, 1H), 3.57 (d, J=12.4 Hz, 1H), 3.48-3.39 (m, 1H), 3.37-3.18 (m, 2H), 2.15 (d, J=13.5 Hz, 1H), 1.82-1.66 (m, 4H), 1.50-1.43 (m, 1H), 1.39 (d, J=7.2 Hz, 3H).

Prepare the following compounds essentially by the method of Example 1, using the appropriate methyl esters in place of methyl 4-[(1S)-1-[[(2R)-1-(2-phenoxyethyl)piperidine-2-carbonyl]amino]ethyl]benzoate:

| Example No. | Chemical Name | Structure | MS (m/z) |
|---|---|---|---|
| 2 | 4-[[[(2R)-1-(2-phenoxyethyl)piperidine-2-carbonyl]amino]methyl]benzoic acid hydrochloride | 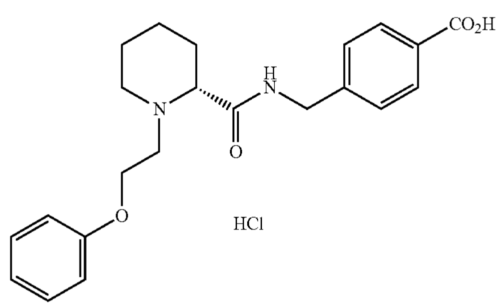 [SMILES: O=C(O)c1ccc(CNC(=O)[C@H]2CCCCN2CCOc2ccccc2)cc1 ; Cl] | 383 (M + H)$^+$ |

-continued

| Example No. | Chemical Name | Structure | MS (m/z) |
|---|---|---|---|
| 3 | 4-[(1S)-1-[[(2R)-1-(2-phenoxyethyl)piperidine-2-carbonyl]amino]propyl]benzoic acid hydrochloride | 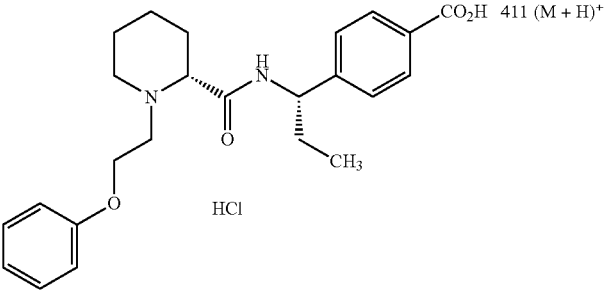 | 411 (M + H)+ |
| 4 | 4-[1-[[(2R)-1-(2-phenoxyethyl)piperidine-2-carbonyl]amino]cyclopropyl]benzoic acid hydrochloride | 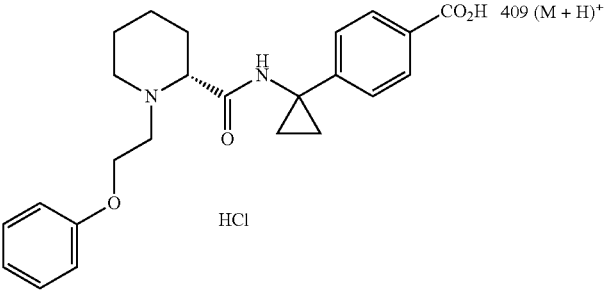 | 409 (M + H)+ |
| 5 | 4-[(1S)-1-[[(2R)-1-(2-(4-fluorophenoxy)ethyl)piperidine-2-carbonyl]amino]ethyl]benzoic acid hydrochloride | 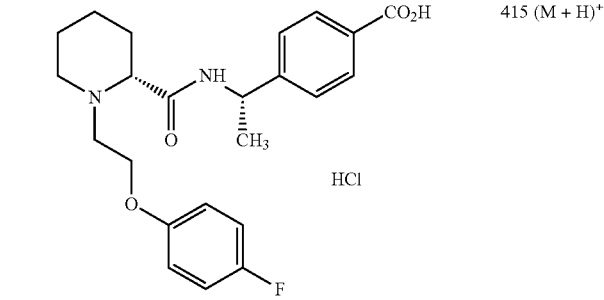 | 415 (M + H)+ |
| 6 | 4-[(1S)-1-[[(2R)-1-(2-(4-cyanophenoxy)ethyl)piperidine-2-carbonyl]amino]ethyl]benzoic acid hydrochloride | 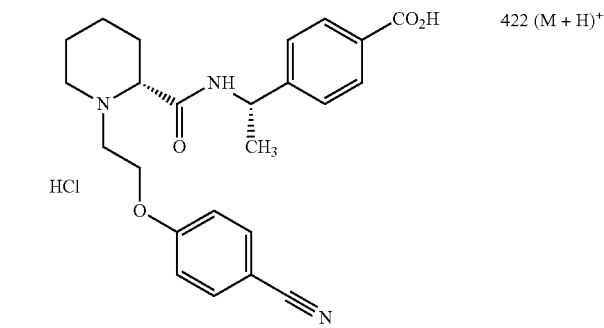 | 422 (M + H)+ |
| 7 | 4-[(1S)-1-[[(2R)-1-(2-(2-methylphenoxy)ethyl)piperidine-2-carbonyl]amino]ethyl]benzoic acid hydrochloride | 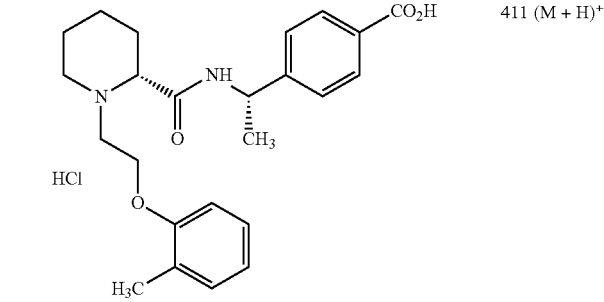 | 411 (M + H)+ |

-continued

| Example No. | Chemical Name | Structure | MS (m/z) |
|---|---|---|---|
| 8 | 4-[(1S)-1-[[(2R)-1-(2-cyclohexyloxyethyl)piperidine-2-carbonyl]amino]ethyl]benzoic acid hydrochloride | 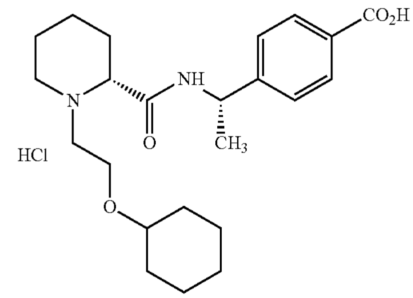 [SMILES: Cl ; C[C@H](NC(=O)[C@H]1CCCCN1CCOC1CCCCC1)c1ccc(C(=O)O)cc1] | 403 (M + H)+ |

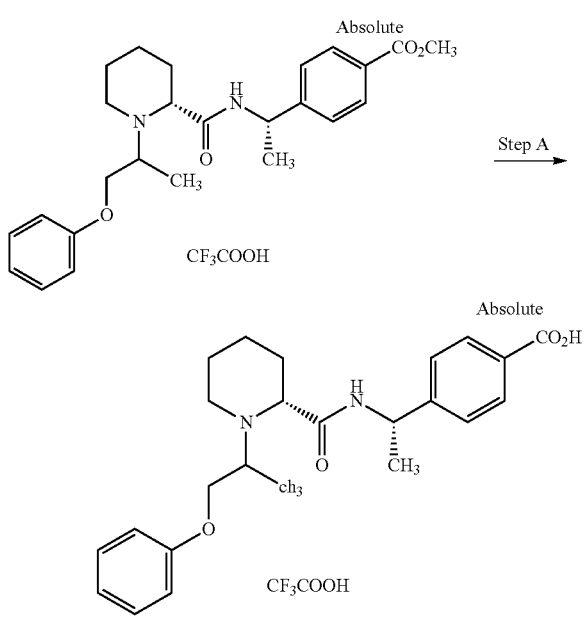

EXAMPLE 9

Synthesis of 4-[(1S)-1-[[(2R)-1-(1-methyl-2-phenoxyethyl)piperidinium-carbonyl]amino]ethyl]benzoic acid trifluoroacetate

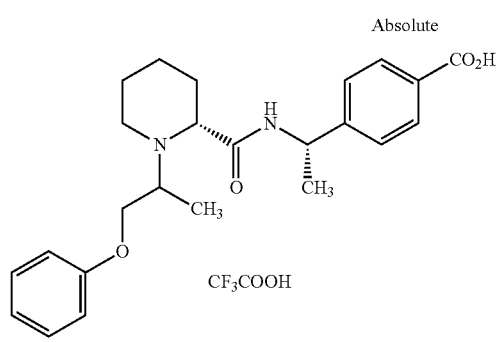 [SMILES: CC(COc1ccccc1)N1CCCC[C@@H]1C(=O)N[C@@H](C)c1ccc(C(=O)O)cc1 ; "CF3COOH"]

Scheme 12, Step A:

Dissolve methyl 4-[(1S)-1-[[(2R)-1-(1-methyl-2-phenoxyethyl)piperidinium-2-carbonyl]amino]ethyl]benzoate trifluoroacetate (24 mg, 0.045 mmol) in THF (226 μL) and treat the mixture with methanol (226 μL) and sodium hydroxide (1 N aqueous solution, 170 μL, 0.17 mmol). Stir the mixture overnight at room temperature, then concentrate under reduced pressure to furnish a gummy solid. Subject the crude material to reverse-phase chromatography on C18 silica gel, eluting with 0.1% TFA in a gradient of 5% to 50% ACN/water to furnish two separate fractions, each containing a separate diastereomer of product. Concentrate each fraction under reduced pressure, dissolve each in a minimal volume of methanol, triturate each with diethyl ether (5 mL), and concentrate each under reduced pressure to furnish Isomer 1 (3.0 mg, 13% yield) and Isomer 2 (1.1 mg, 5% yield) of the title compound as white solids.

EXAMPLE 9a

Major Isomer (Isomer 1)

Mass spectrum (m/z): 411 (M+H)+. $^1$H NMR (DMSO-$d_6$) δ 9.75 (br s), 9.30 (d, J=7.4 Hz, 1H), 7.82 (d, J=7.6 Hz, 2H), 7.43 (d, J=7.6 Hz, 2H), 7.33-7.25 (m, 2H), 7.04-6.95 (m, 3H), 5.03 (app p, J=6.8 Hz, 1H), 4.35-4.24 (m, 2H), 4.07 (dd, J=12.1, 3.5 Hz, 1H), 3.74-3.65 (m, 1H), 3.52 (br d, J=12.5 Hz, 1H), 3.11-2.99 (m, 1H), 2.15 (br d, J=12.4 Hz, 1H), 1.89-1.71 (m, 4H), 1.52-1.45 (m, 1H), 1.40 (d, J=6.8 Hz, 3H), 1.33 (d, J=6.8 Hz, 3H).

EXAMPLE 9b

Minor Isomer (Isomer 2)

Mass spectrum (m/z): 411 (M+H)+.

It is readily appreciated by one of ordinary skill in the art that the HCl salts of examples 1-9 are readily converted to the corresponding free bases utilizing conditions well known in the art.

In Vitro Binding to Human EP1, EP2, EP3, and EP4 hEP1 and hEP4 membranes are prepared from recombinant HEK293 cells stably expressing the human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

$K_d$ values for [3H]-PGE$_2$ binding to each receptor are determined by saturation binding studies or homologous competition. Compounds are tested in a 96-well format using a three-fold dilution series to generate a 10-point curve. Diluted compound is incubated with 20 µg/well EP1, 10 µg/well EP2, 1 ug/well EP3 or 10 to 20 µg/well EP4 membrane for 90 minutes at 25° C. in the presence of 0.3 to 0.5 nM [$^3$H]-PGE$_2$ (PerkinElmer, 118 to 180 Ci/mmol). The binding reaction is performed in 200 µL MES buffer (10 mM MES pH 6.0 with KOH, 10 mM MgCl$_2$ and 1 mM EDTA) using 0.5 mL polystyrene 96-well deep-well plates. Nonspecific binding is calculated by comparing binding in the presence and absence of 2 µM of PGE$_2$. The membranes are harvested by filtration (TomTek harvester), washed 4 times with cold buffer (10 mM MES pH 6.0 with KOH, 10 mM MgCl$_2$), dried in a 60° C. oven, and the radioactivity is quantified as counts per minute (CPM) using a TopCount detector. Percent specific binding is calculated as the percent of the binding in the absence of any inhibitor, corrected for binding in the presence of 2 µM of PGE$_2$. Data are analyzed using a 4-parameter nonlinear logistic equation (ABase Equation 205) as shown: $y=(A+((B-A)/(1+((C/x)^D))))$ where, y=% specific inhibition, A=bottom of the curve; B=top of the curve; C=relative IC$_{50}$=concentration causing 50% inhibition based on the range of the data from top to bottom; D=Hill Slope=slope of the curve. $K_i$ conversion from IC$_{50}$ Values ($K_i=IC_{50}/(1+[L]/K_d)$ where [L] is the ligand concentration). The compounds of Examples 1-9 herein are tested essentially as described above and exhibit a $K_1$ value for hEP4 of lower than about 1 µM.

TABLE 1

In vitro binding of Example 1 to human EP1, EP2, EP3 and EP4

| Test Compound | hEP1, $K_i$ (nM) | hEP2, $K_i$ (nM) | hEP3, $K_i$ (nM) | hEP4, $K_i$ (nM) |
|---|---|---|---|---|
| Example 1 | >17500 | 1550 ± 1860 (n = 3) | >14000 | 54 ± 27 (n = 7) |

More specifically, following the procedures essentially as described above, the data in table 1 demonstrate that the compound of Example 1 binds to hEP4 at low nanomolar concentrations. The data in table 1 also demonstrate the compound of Example 1 binds to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 µg/mL geneticin and 2 mM L-glutamine. Confluent cultures are grown at 37° C. in an atmosphere containing 5% CO$_2$. Cells are harvested using 2.5% Trypsin-EDTA, suspended in freeze media (FBS with 6% DMSO) at 10$^7$ cells/mL and aliquots are stored in liquid nitrogen. Just before assay, cells are thawed in DMEM, centrifuged, and resuspended in cAMP buffer.

The inhibition of PGE$_2$-stimulated cAMP production by EP4 antagonists is measured using HTRF (Cisbio catalogue #62AM4PEB). An aliquot equivalent to 4000 cells is incubated with 50 µL cAMP assay buffer containing PGE$_2$ in a concentration predetermined to produce an EC$_{80}$ (0.188 nM PGE$_2$ from Sigma, catalog #P5640-10 mg) and EP4 antagonists at room temperature for 20 minutes. cAMP assay buffer contains 500 mL HBSS, 0.1% BSA, 20 mM HEPES and 200 µM IBMX (Sigma I5879). CJ-042794 (4-{(1S)-1-[({5-chloro-2-[(4-fluorophenyl)oxy]phenyl}carbonyl)amino]ethyl}benzoic acid) serves as a positive control. To measure the cAMP levels, cAMP-d2 conjugate and anti cAMP-cryptate conjugate in lysis buffer are incubated with the treated cells at room temperature for 1 hour. The HTRF signal is detected using an EnVision® plate reader (Perkin-Elmer) to calculate the ratio of fluorescence at 665 nm to that at 620 nm. The raw data are converted to cAMP amount (pmol/well) using a cAMP standard curve generated for each experiment. Data are analyzed using a 4-parameter nonlinear logistic equation (ABase Equation 205) as shown: $y=(A+((B-A)/(1+((C/x)^D))))$ where, y=% specific inhibition, A=Bottom of the curve, B=Top of the curve, C=Relative IC$_{50}$=concentration causing 50% inhibition based on the range of the data from top to bottom, D=Hill, Slope=slope of the curve.

Following the procedures essentially as described above, the compounds of Examples 1-9 herein are tested essentially as described above and exhibit an IC$_{50}$ of lower than about 1 µM. More specifically, following the procedures essentially as described above, Example 1 has an IC$_{50}$ of 6.9±2.5 nM (n=5) measured at human EP4. This demonstrates that the compounds of Examples 1-9 are potent antagonists of human EP4 in vitro.

In Vitro Rat EP4 Functional Antagonist Activity

Rat EP4 cDNA (Genebank Accession# NM_03276) is cloned into pcDNA 3.1 vector and subsequently transfected in HEK293 cells for receptor expression. Rat EP4 stable clone is scaled up and then frozen down as cell bank for future compounds screening. To test EP4 antagonist compounds in rEP4 cells, thaw the frozen cells and then resuspend cells in cAMP assay buffer. The cAMP buffer is made by HBSS without Phenol Red (Hyclone, SH30268) supplemented with 20 mM HEPES (Hyclone, SH30237), 0.1% BSA (Gibco, 15260) and 125 µM BMX (Sigma, I5879). The cells are plated into 96-well half area flat-bottom polystyrene black plates (Costar 3694). Compounds are serially diluted with DMSO to give 10-point concentration response curves. Then diluted compounds are added into cAMP assay buffer which contains PGE$_2$ (Cayman 14010, in a concentration predetermined to produce an EC$_{80}$) at ratio of DMSO/buffer at 1/100. The cells are treated with compounds in the presence of PGE$_2$ (EC$_{80}$ concentration) for 30 minutes at room temperature. The cAMP levels generated from the cells are quantified by a cAMP HTRF assay kit (Cisbio 62AM4PEC). The plates are read on an EnVision plate reader using HTRF optimized protocol (PerkinElmer). IC$_{50}$s are calculated using Graphpad Prism (v. 4) nonlinear regression, sigmoidal dose response curve fitting.

Following the procedures essentially as described above, the compounds of Examples 1-9 herein are tested essentially as described above and exhibit an IC$_{50}$ of lower than about 1 µM. More specifically, following the procedures essentially as described above, the compound of Example 1 has an IC$_{50}$ of 15 nM measured at rat EP4. This demonstrates that the compounds of Examples 1-9 are a potent antagonists of rat EP4 ire vitro.

In Vitro Antagonist Activity in Human Whole Blood

The inhibitory effects of $PGE_2$ on LPS-induced TNFα production from macrophages/monocytes are believed to be mediated by EP4 receptors (See Murase, A., et al., Life Sciences, 82:226-232 (2008)). The ability of the compound of Example 1 to reverse the inhibitory effect of $PGE_2$ on LPS-induced TNFα production in human whole blood is an indicium of functional activity.

Blood is collected from normal volunteer donors into sodium heparin vacutainer tubes. Donors have not taken NSAIDs or celecoxib within 48 hours or glucocorticoids within two weeks prior to the donation. All tubes/donor are pooled into 50 mL Falcon conical centrifuge tubes and 98 μL/well is distributed into 96-well tissue culture plates (Falcon 3072). Compounds are diluted into DMSO to 100× final and 1 μL/well in triplicate is added to the blood to give 7-point concentration response curves. The blood is pretreated with the compounds at 37° C., in a 5% $CO_2$ humidified atmosphere, for 30 minutes, after which 1 μL/well of a solution of 1 mg/mL of lipopolysaccharide (LPS) (Sigma 0111:B4) in 0.2 mg/mL bovine serum albumin (BSA)/PBS both with and without 1 mM $PGE_2$ (Cayman 14010) is added to give a final LPS concentration of 10 μg/mL both with and without 10 nM $PGE_2$. The plates are incubated for 20-24 hours at 37° C. in a 5% $CO_2$, humidified atmosphere. The plates are centrifuged at 1800×g for 10 minutes at 22° C., in an Eppendorf 5810R centrifuge. Plasma is removed from the cell layer and is transferred to v-bottom polypropylene plates. TNFα levels in 2 μL plasma are quantified by a commercially available enzyme immunoassay (R&D Systems DY210), using Immulon 4 HBX plates (Thermo 3855) and 3,3',5,5' tetramethylbiphenyl-4,4'-diamine substrate (KPL 50-76-03). The plates are read at $A_{450}$-$A_{650}$ on a plate reader (Molecular Devices Versamax) using SOFTmaxPRO (v. 4.3.1) software. $IC_{50}$s are calculated using Graphpad Prism (v. 4) nonlinear regression, with sigmoidal dose response curve fitting. Results are expressed as the geometric mean±standard deviation; n=number of independent determinations.

Following the procedures essentially as described above, the compounds of Examples 1-9 herein were tested essentially as described above and exhibited an $IC_{50}$ of lower than about 1 μM. More specifically, following the procedures essentially as described above, compound of Example 1 has an $IC_{50}$ of 123±88 nM (n=12). This demonstrates that the compounds of Examples 1-9 are potent EP4 antagonists in the human blood TNFα induction assay.

We claim:
1. A pharmaceutical composition, comprising a compound of the formula:

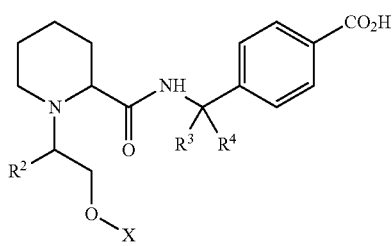

wherein X is:

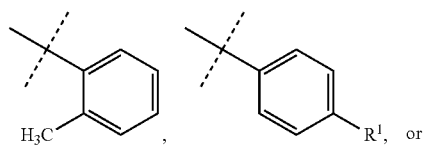

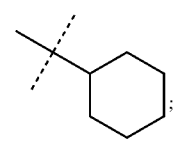

$R^1$ is H, —CN, or F;
$R^2$ is H or methyl;
$R^3$ is H; and
$R^4$ is H, methyl, or ethyl; or
$R^3$ and $R^4$ joined together form a cyclopropyl ring;
or a pharmaceutically acceptable salt thereof, in combination with one or more pharmaceutically acceptable carriers, diluents, or excipients.

2. The pharmaceutical composition according to claim 1 wherein the compound is:

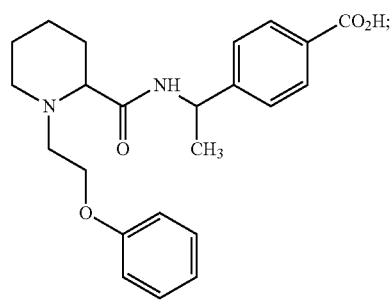 [SMILES: CC(NC(=O)C1CCCCN1CCOc1ccccc1)c1ccc(C(=O)O)cc1]

or a pharmaceutically acceptable salt thereof.

3. The pharmaceutical composition according to claim 2 wherein the compound is:

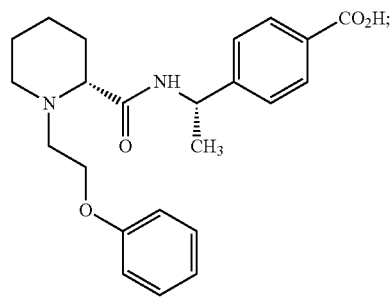 [SMILES: C[C@H](NC(=O)[C@H]1CCCCN1CCOc1ccccc1)c1ccc(C(=O)O)cc1]

or a pharmaceutically acceptable salt thereof.

4. The pharmaceutical composition according to claim 3 wherein the compound is:
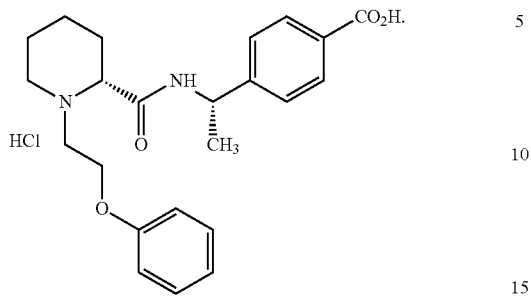
* * * * *